United States Patent [19]

Yagawara et al.

[11] Patent Number: 5,019,885
[45] Date of Patent: May 28, 1991

[54] GAS DETECTING DEVICE

[75] Inventors: Shinji Yagawara; Wasaburo Ohta, both of Yokohama, Japan

[73] Assignee: Ricoh Company, Ltd., Tokyo, Japan

[21] Appl. No.: 500,600

[22] Filed: Mar. 28, 1990

[30] Foreign Application Priority Data

Mar. 30, 1989 [JP] Japan .................................. 1-80179
Jul. 7, 1989 [JP] Japan ................................ 1-175790

[51] Int. Cl.⁵ ..................... H01L 29/66; H01L 29/96; H01L 27/02; H01C 7/00
[52] U.S. Cl. ........................................ 357/25; 357/51; 338/25; 338/34; 338/308
[58] Field of Search ..................... 357/25, 26, 28, 25; 338/25, 34, 308

[56] References Cited

U.S. PATENT DOCUMENTS 4,624,137 11/1986 Johnson et al. ..................... 338/25
4,654,624 3/1987 Hagen et al. ........................ 338/25
4,706,061 11/1987 Johnson .............................. 338/34

FOREIGN PATENT DOCUMENTS 169519A 1/1986 European Pat. Off. .............. 357/25
61-191953 8/1986 Japan .
01100445 4/1989 Japan .................................... 357/25

Primary Examiner—Rolf Hille
Assistant Examiner—Mahshid Saadat
Attorney, Agent, or Firm—Oblon, Spivak, McClelland, Maier & Neustadt

[57] ABSTRACT

A gas detecting device includes a substrate and a plurality of gas sensitive elements supported by the substrate. A plurality of predetermined temperatures at which gases are detected are provided. The gas detecting device also includes a plurality of pairs of electrode leads supported by the substrate, each of the plurality of pairs of electrodes being connected to a corresponding one of the gas sensitive elements, and heater leads that are supported by the substrate and heat the plurality of gas sensitive elements so that each of the gas sensitive elements is set at a corresponding one of the plurality of predetermined temperatures.

16 Claims, 7 Drawing Sheets

GAS DETECTING DEVICE

BACKGROUND OF THE INVENTION

The present invention generally relates to a gas detecting device that detects the presence of a plurality of different kinds of gases.

As is known, various types of gas detecting devices have been proposed. For example, Japanese Laid-Open Patent Application No. 61-191953 discloses a gas detecting device in which a microheater formed by fine formation is used. The proposed gas detecting device has a single gas sensitive element, which is heated by a heater. The proposed gas detecting device is designed to detect a single kind of gas. It is possible that an output signal from the single gas sensitive element could be filtered by a filter which is attached to the gas detecting element. However, it is impossible to obtain output signals corresponding to different kinds of gases from the single gas sensitive element.

In order to detect the presence of different kinds of gases, it is possible that individual gas sensitive elements sensitive to different kinds of gas be used. However, the use of different gas sensitive elements leads to an increase in the manufacturing cost.

SUMMARY OF INVENTION

A general object of the present invention is to provide a gas detecting device in which the aforementioned disadvantages are eliminated.

A more specific object of the present invention is to provide a gas detecting device capable of detecting the presence of different kinds of gases.

The above-mentioned objects of the present invention are achieved by a gas detecting device comprising a substrate; a plurality of gas sensitive elements supported by the substrate, a plurality of predetermined temperatures at which gases that are detected being provided; a plurality of pairs of electrode leads supported by the substrate, each of the plurality of pairs of electrodes being connected to a corresponding one of the gas sensitive elements; and heater means supported by the substrate, for heating the plurality of gas sensitive elements so that each of the gas sensitive elements is set at a corresponding one of the plurality of predetermined temperatures.

Further objects, features and advantages of the present invention will become apparent from the following detailed description when read in conjunction with the accompanying drawings.

DESCRIPTION OF THE PREFERRED EMBODIMENTS

Figure 1:
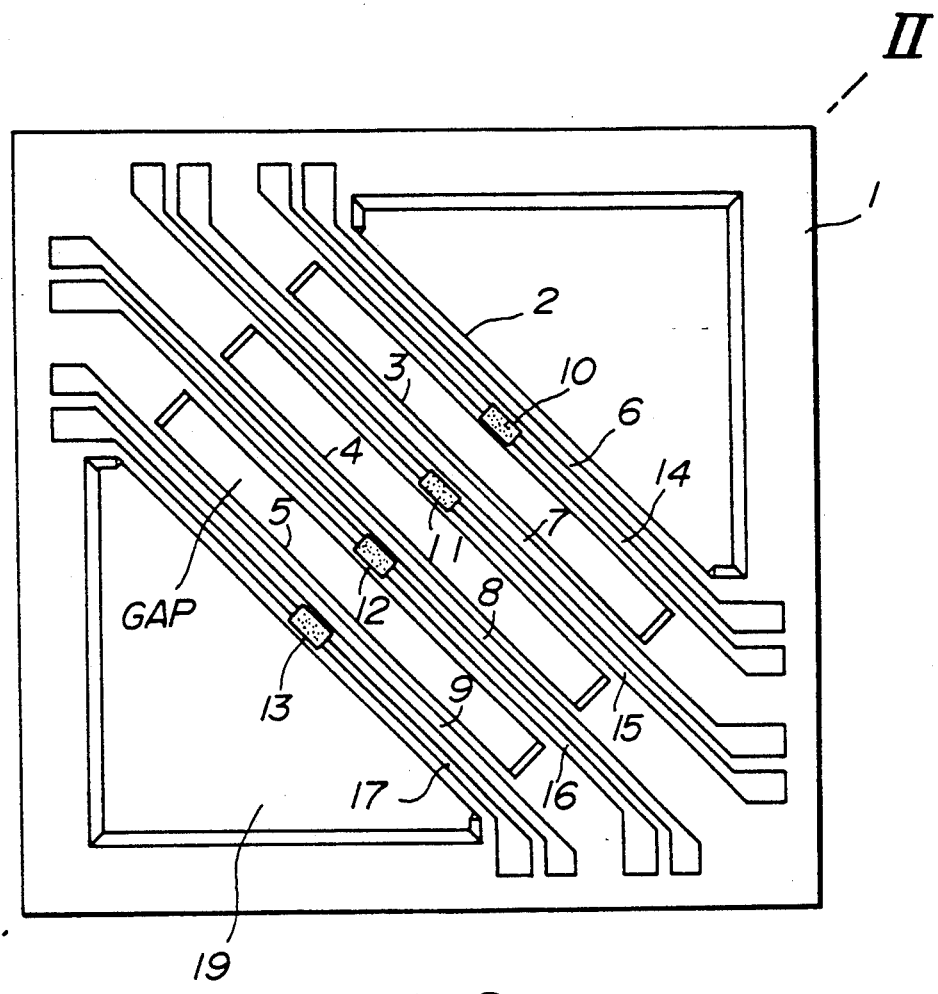
FIG. 1 is a plan view of a gas detecting device according to a first preferred embodiment of the present invention.
Figure 2:
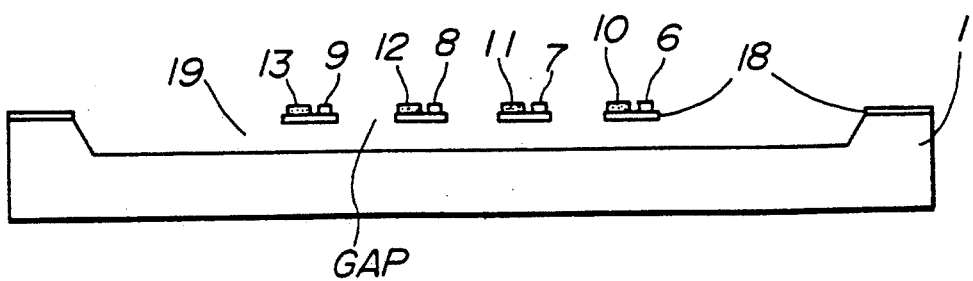
FIG. 2 is a cross sectional view taken along the line II—II shown in FIG. 1.

A description will now be given of a first preferred embodiment of the present invention. FIG. 1 is a plan view of a gas detecting device according to the first preferred embodiment of the present invention, and FIG. 2 is a cross sectional view taken along the line II—II shown in FIG. 1. A substrate 1 is of a substantially square shape and has a groove 19. The shape of the substrate 1 is not, however, limited to a square shape. Four bridge portions 2, 3, 4 and 5, each made of an insulating film 18, are formed across the groove 19 and diagonally connect corner portions of the substrate 1. Heater leads 6, 7, 8 and 9 are formed on the bridge portions 2, 3, 4 and 5, respectively. A pair of electrode leads 14 is formed on the insulating film 18 of the bridge portion 2 so that each of the electrode leads 14 is aligned in a parallel manner with the heater lead 6. Similarly, pairs of electrode leads 15, 16 and 17 are formed on the bridge portions 3, 4 and 5, respectively. Opposite ends of the pair of electrode leads 14 are spaced apart from each other. A gas sensitive element 10 is formed on the bridge portion 2 so that it covers the opposite ends of the heater leads 14. Similarly, gas sensitive elements 11, 12 and 13 are formed on the bridge portions 3, 4 and 5, respectively, so that they cover opposite portions of the pairs of electrode leads 15, 16 and 17, respectively.

It is preferable that the substrate 1 be formed of a material which is not deformable at high temperatures and which is easily etchable by an under-cut etching process, such as either silicon (Si), aluminum (Al), copper (Cu), nickel (Ni) or chromium (Cr). It is further preferable to use the (100) plane of silicon because it is easily etchable by an under-cut etching process based on anisotropic etching. The groove 19 is formed by anisotropic etching. Each of the side ends of the substrate 1 has a length between 1 mm and 4 mm and a thickness between 0.1 mm and 1 mm. The insulating layer 18 is made of either silicon dioxide ($SiO_2$), alumina ($Al_2O_3$), silicon nitride ($Si_3N_4$), tantalum oxide ($TaO_5$) or so on.

The heater leads 6, 7, 8 and 9 are formed of either platinum (Pt), palladium (Pd), gold (Au), irridium (Ir), rhodium (Rh), nickel chromium (NiCr), tantalum nitride ($Ta_2N$), silicon carbon (SiC), kanthal or the like. Similarly, the electrode leads 14, 15, 16 and 17 are formed of either platinum (Pt), palladium (Pd), gold (Au), irridium (Ir), rhodium (Rh), nickel chromium (NiCr), tantalum nitride ($Ta_2N$), silicon carbon (SiC), kanthal or the like. The insulating layer 18 is made of either silicon dioxide ($SiO_2$), alumina ($Al_2O_3$), silicon nitride ($Si_3N_4$), tantalum oxide ($TaO_5$) or so on. Alternatively, each of the heater leads 6–9 and/or electrode leads 14–17 may have a multilayer structure in which the above-mentioned heater lead is sandwiched between adhesion reinforcement layers each containing either nickel (N), tungsten (W), molybdenum (Mo), chromium (Cr), titanium (Ti) or the like.

The gas sensitive elements 10–13 are formed of a metal oxide semiconductor material containing either tin (Sn), zinc (Zn), titanium (Ti), indium (In), nickel (Ni), tungsten (W), cadmium (Cd), or vanadium (V). It is particularly preferable to use tin. The deposition of the gas sensitive elements 10–13 is carried out by a conventional process such as an evaporation process, a sputtering process or a process disclosed in Japanese Laid-Open Patent Application No. 59-89763.

Figure 3:
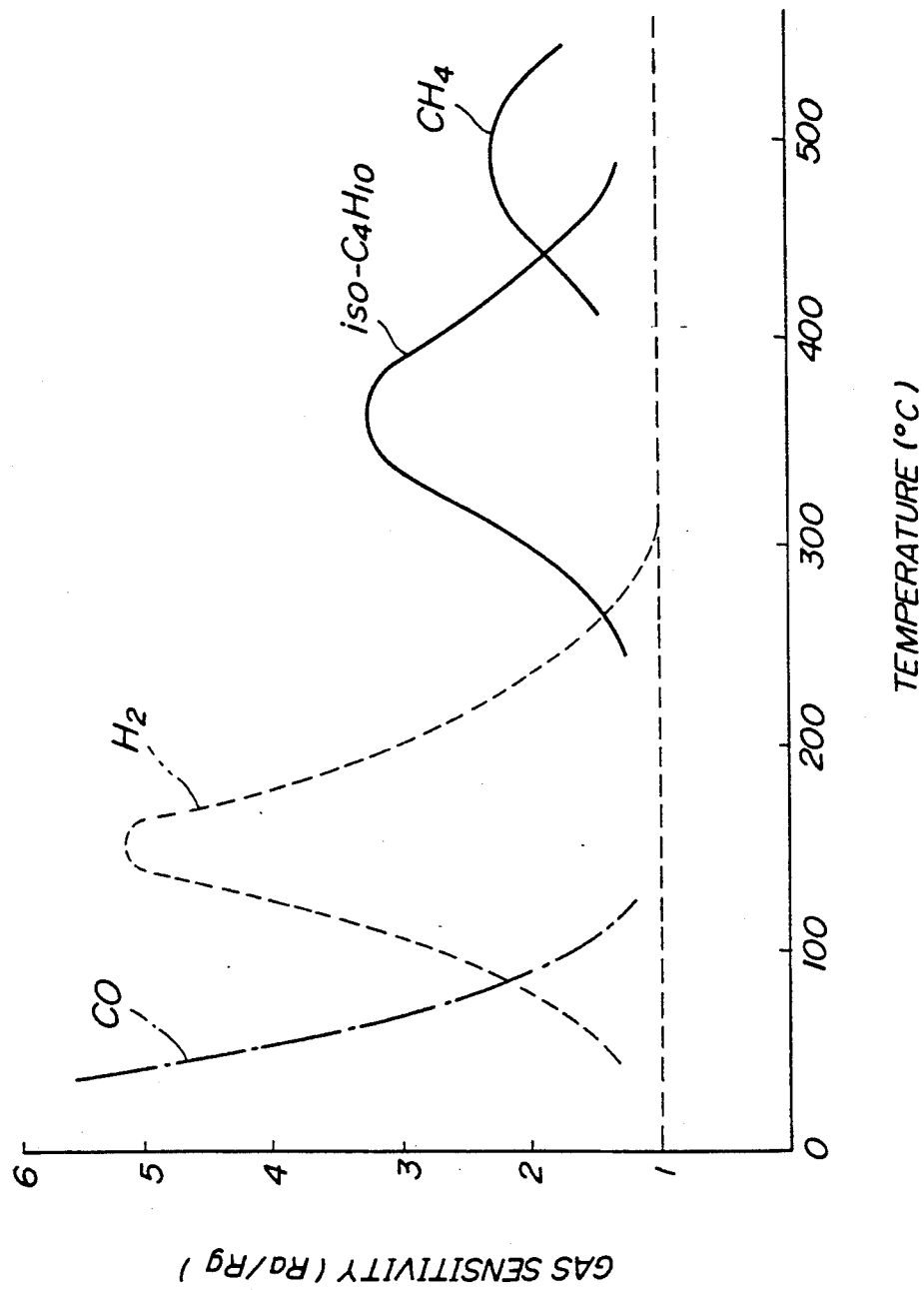
FIG. 3 is a graph showing the relationship between gas sensitivity of a metal oxide semiconductor material and temperature.

FIG. 3 is a graph illustrating gas sensitivity vs. temperature characteristics of a metal oxide semiconductor layer formed by the process disclosed in Japanese Laid-Open Patent Application No. 59-89763. Gas sensitivity of the formed metal oxide semiconductor layer is represented by Ra/Rg wherein Ra is a resistance value of the metal oxide semiconductor layer in air, and Rb is a resistance value thereof in a gas. A temperature at which a maximum sensitivity value is obtained varies depending on the kind of gas. Thus, the gas sensitive elements 10, 11, 12 and 13 are heated to mutually different temperatures by the heater leads 6, 7, 8 and 9, respectively. For example, when the gas sensitive elements 10, 11, 12 and 13 are set to room temperatures, 150° C., 370° C. and 500° C., respectively, CO, $H_2$, iso-$C_4H_{10}$ and $CH_4$ gases are detected, respectively. Of course, different kinds of gases can be detected when the gas sensitive elements 10–13 are set to different room temperatures. The temperatures of the gas sensitive elements 10, 11, 12 and 13 are controlled by adjusting the amount of each current passing through the heater leads 6, 7, 8 and 9, respectively. In the experiments, the gas sensitive layer is between 450°–500° C. when a current between 20–30 mA passes through the corresponding heater lead.

It is possible to form the aforementioned element on a single bridge portion connecting the diagonal corners of the substrate 1. However, the structure shown in FIG. 1 is preferred to this above structure because a gap formed in the insulating film 18 for separating neighboring heater leads prevents heat from being directly conducted.

It is possible to set two of the four gas sensitive elements 10–13 at a first temperature, and set at the remaining two gas sensitive elements at a second temperature. It is also possible to select any combination of temperatures and gas sensitive elements 10–13, depending on what kinds of gases are to be detected.

Figure 4:
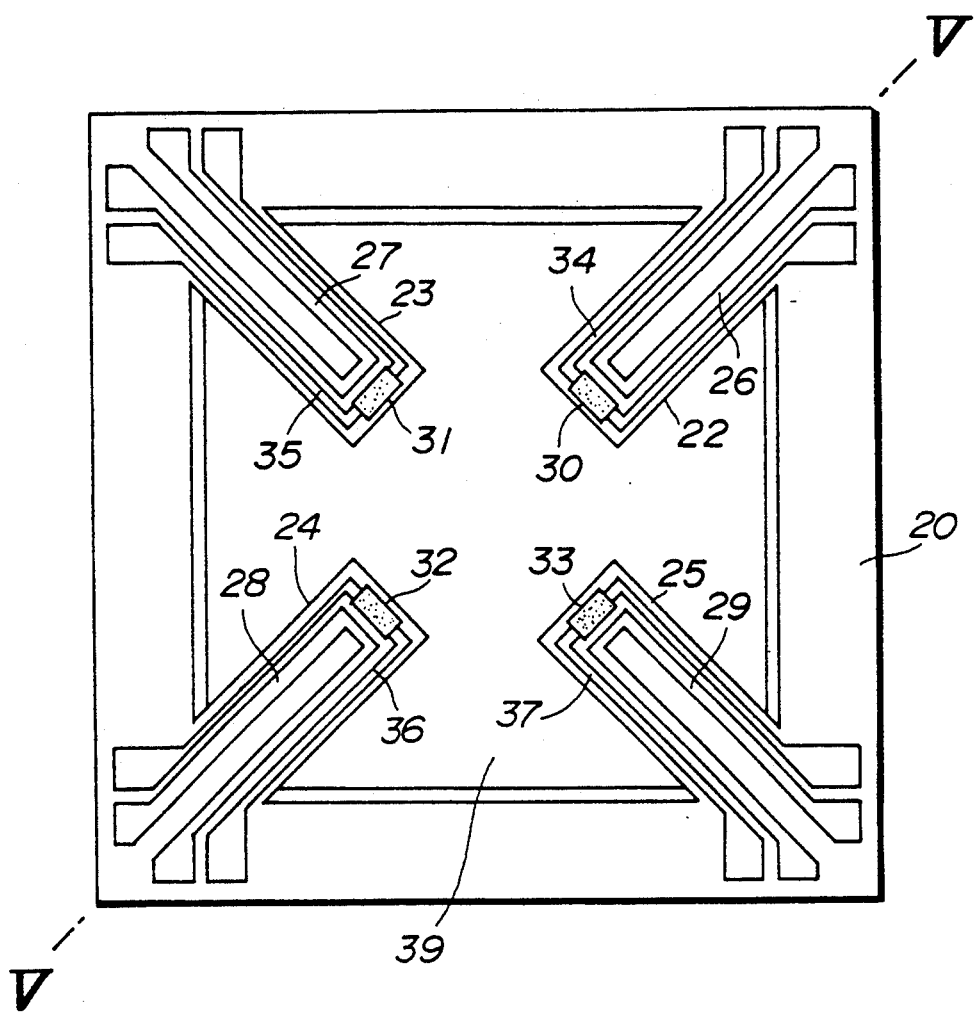
FIG. 4 is a plan view of a gas detecting device according to a second preferred embodiment of the present invention.
Figure 5:
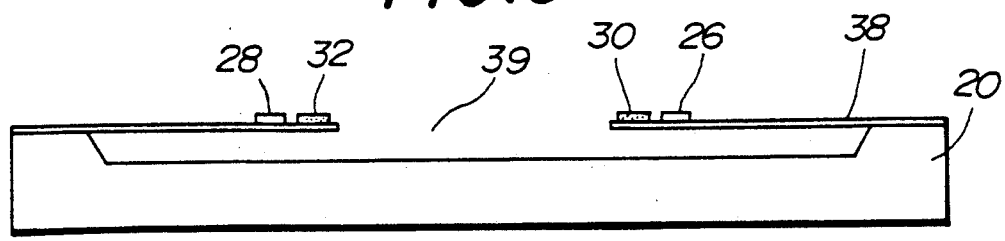
FIG. 5 is a cross sectional view taken along the line V—V shown in FIG. 4.

FIG. 4 is a plan view of a gas detecting device according to a second preferred embodiment of the present invention, and FIG. 5 is a cross sectional view taken along the line V—V shown in FIG. 4. A substrate 20 is of a substantially square shape and has a groove 39. Four cantilever portions 22, 23, 24 and 25 each formed of an insulating film 38, diagonally extend from the corner portions of the substrate 20 and are above the groove 39. A pair of electrode leads 34 is formed on the cantilever portion 22 along sides thereof. Similarly, pairs of electrode leads 35, 36 and 37 are formed on the cantilever portions 23, 24 and 25 along sides thereof, respectively. Opposite ends of the electrode leads 34 are spaced apart from each other. A gas sensitive element 30 is formed on the cantilever portion 22 so that it covers the opposite ends of the electrode leads 34. Similarly, gas sensitive elements 31, 32 and 33 are formed on the cantilever portions 23, 24 and 25 so that they cover opposite ends of the electrode leads 35, 36 and 37, respectively. A heater lead 26 is formed on the cantilever portion 22 along the electrode leads 34. Similarly, heater leads 27, 28 and 29 are formed on the cantilever portions 23, 24 and 25 along the electrode leads 35, 36 and 37, respectively. The substrate 20, the insulating layer 38, the heater leads 26–29, the electrode leads 34–37 and gas sensitive elements 30–33 can be formed of any of the aforementioned corresponding materials. The gas sensitive elements 30, 31, 32 and 33 are set at individual temperatures by adjusting currents passing through the heater leads 26, 27, 28 and 29, respectively. Of course, it is possible to select any combination of temperatures and gas sensitive elements 30–33, depending on what kinds of gases are to be detected.

Figure 6:
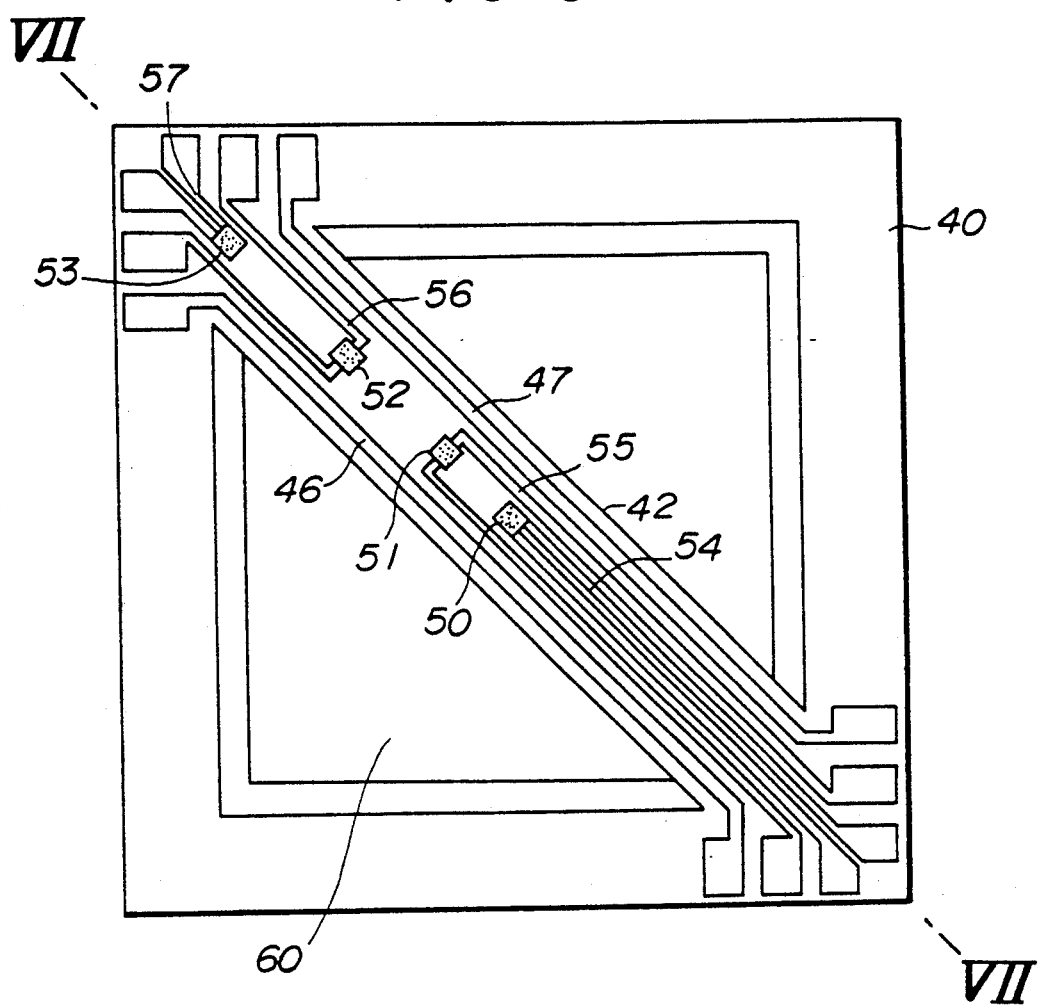
FIG. 6 is a plan view of a gas detecting device according to a third preferred embodiment of the present invention.
Figure 7:
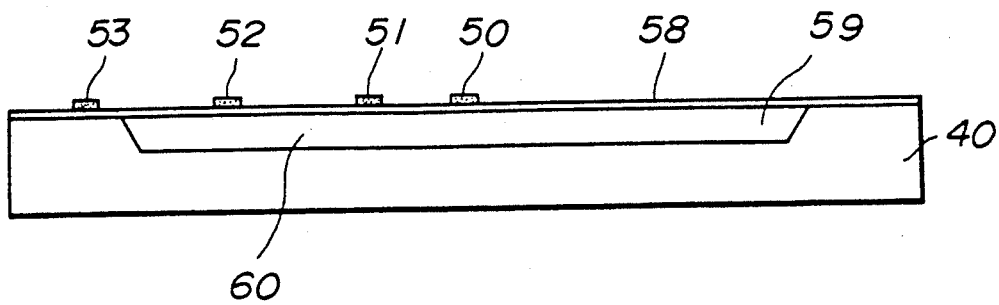
FIG. 7 is a cross sectional view taken along the line VII—VII shown in FIG. 6.

A description will now be given of a gas detecting device according to a third preferred embodiment of the present invention with reference to FIGS. 6 and 7. FIG. 6 is a plan view of the gas detecting device, and FIG. 7 is a cross sectional view taken along the line VII—VII shown in FIG. 6. A substrate 40 is of a substantially square shape and has a groove 60. A single cantilever bridge 42 formed of an insulating film 58 is formed across the groove 60 and diagonally connects two corner portions of the substrate 40. A pair of heater leads 46 and 47 is formed on the bridge portion 42 along opposite sides thereof. Four gas sensitive elements 50, 51, 52 and 53 are spaced apart from each other and arranged into a line between the pair of heater leads 46 and 47. Pairs of electrode leads 54, 55, 56 and 57 are connected to the gas sensitive elements 50, 51, 52 and 53, respectively, and extend in a parallel manner with each other. The pair of the electrode leads 55 is located outside of the pair of electrode leads 54. The pair of electrode leads 57 is located outside of the electrode leads 56.

Figure 8:
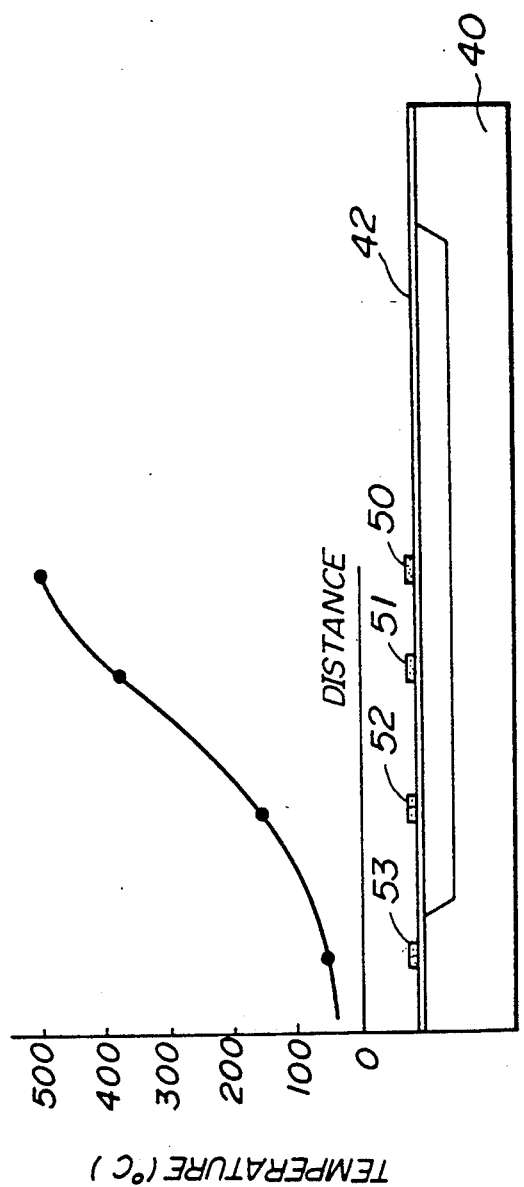
FIG. 8 is a graph illustrating a temperature vs. distance characteristic of the third embodiment of the present invention shown in FIGS. 6 and 7.

FIG. 8 is a graph illustrating the relationship between temperature and distance from the left side of the substrate 40 shown in FIG. 7. It can be seen from the graph of FIG. 8 that when currents pass through the heater leads 46 and 47, the gas sensitive elements 50, 51, 52 and 53 rise to mutually different temperatures. That is, the gas sensitive elements 50–53 are set at temperatures which gradually increase from the left side of the substrate 40 shown in FIG. 8. Thus, the gas sensitive element 50 has the highest temperature and the gas sensitive element 53 has the lowest temperature.

Figure 9:
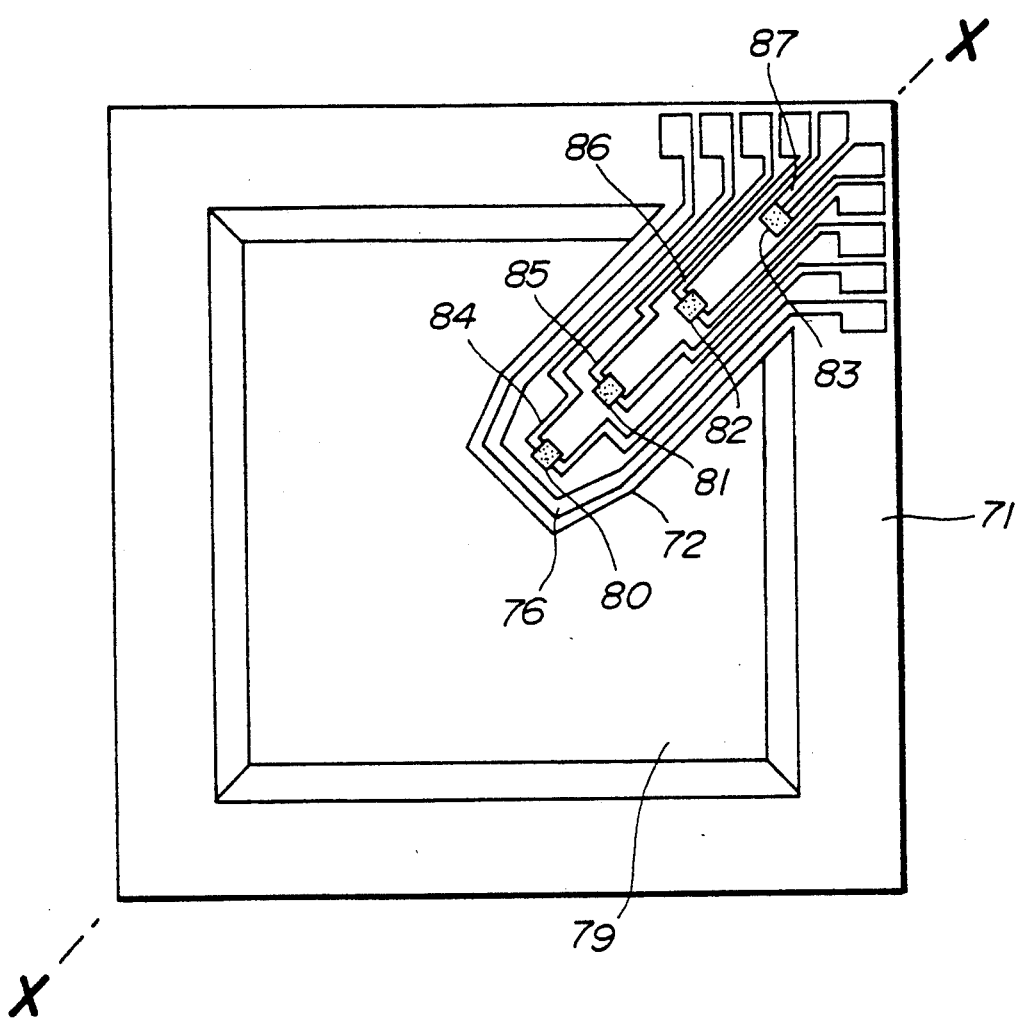
FIG. 9 is a plan view of a gas detecting device according to a fourth embodiment of the present invention.

A description will now be given of a gas detecting device according to a fourth embodiment of the present invention with respect to FIGS. 9 and 10. A substrate 71 is of a substantially square shape and a single cantilever portion 72, which extends from a corner portion of the substrate 71 and which is above a groove 79 formed in the substrate 71. A heater lead 76 is formed on the cantilever portion 72 along the sides thereof. The cantilever portion 72 includes an insulating layer 88. Four gas sensitive elements 80, 81, 82 and 83 are spaced apart from each other and arranged into a line on the cantilever portion 72 and located within an area surrounded by the heater lead 76. A pair of electrode leads 86 extending from the gas sensitive element 82 is arranged outside of a pair of electrode leads 87, which extends from the gas sensitive element 83. A pair of electrode leads 85 extends from the gas sensitive element 81 and is located outside of the pair of electrode leads 86. A pair of electrode leads 84 extends from the gas sensitive element 80 and is located outside of the pair of electrode leads 85.

Figure 10:
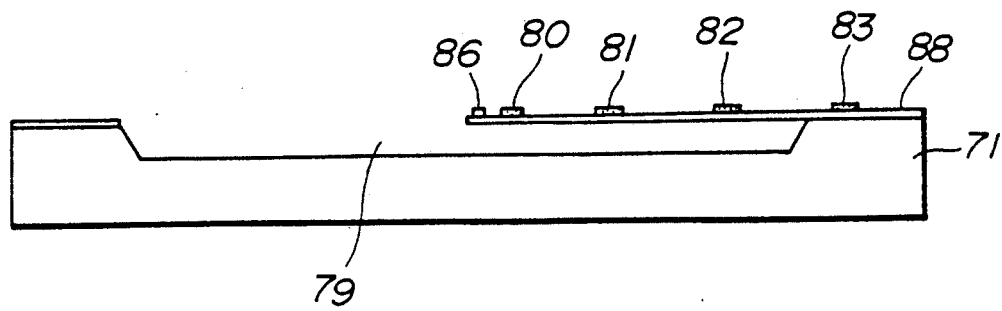
FIG. 10 is a cross sectional view taken along the line X—X shown in FIG. 9.
Figure 11:
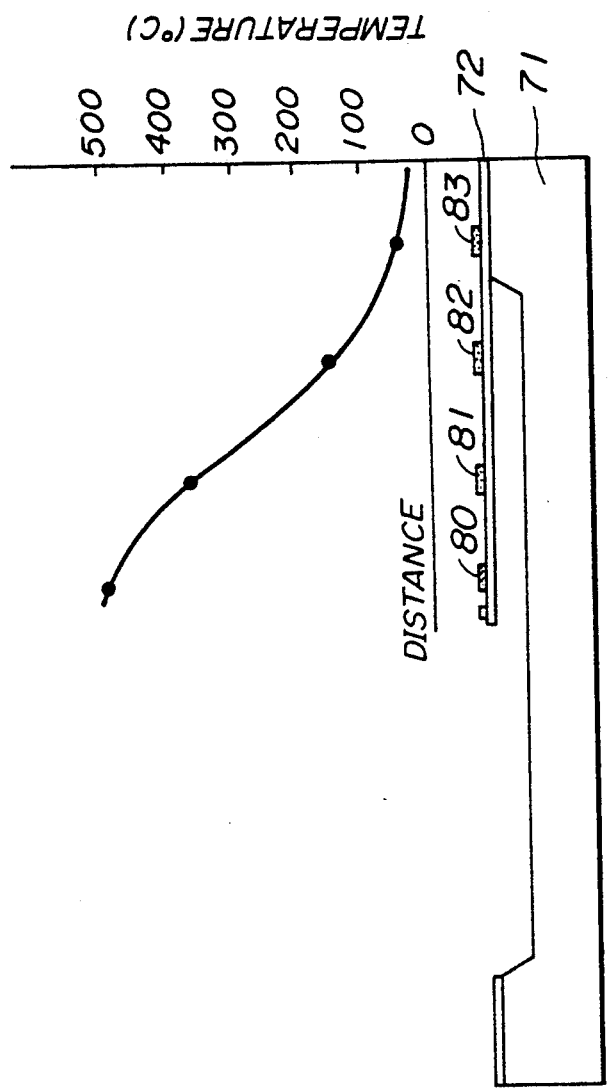
FIG. 11 is a graph showing a temperature vs. distance characteristic of the fourth embodiment of the present invention shown in FIGS. 9 and 10.

FIG. 11 is a graph showing the relationship between temperature and distance from the right side of the substrate 71 shown in FIG. 10. The gas sensitive elements 80-83 rise to temperatures which gradually increase from the right side of the substrate 71. Thus, the gas sensitive element 80 has the highest temperature and the gas sensitive element 83 has the lowest temperature.

The number of gas sensitive elements is not limited to the specifically described embodiments. Similarly, the structures of the substrate, bridge portions and cantilever portions are not limited to the aforementioned embodiments. An insulating layer may be formed on the entire surface of the device except for the gas sensitive elements.

The present invention is not limited to the specifically described embodiments, and variations and modifications may be made without departing from the scope of the present invention.

What is claimed is:

1. A gas detecting device comprising:
    a substrate;
    a plurality of gas sensitive elements supported by said substrate and spaced apart from each other, said gas sensitive elements having respective predetermined temperatures at which gases are most effectively detected;
    a plurality of pairs of electrode leads supported by said substrate, each of said plurality of pairs of electrode leads being connected to a corresponding one of said gas sensitive elements; and
    heater means supported by said substrate, for heating said plurality of gas sensitive elements so that each of said gas sensitive element is set at a corresponding one of said plurality of predetermined temperatures.

2. A gas detecting device as claimed in claim 1, wherein:
    said substrate has a groove formed at a center portion thereof and a plurality of bridge portions formed across said groove;
    each of said plurality of gas sensitive elements is formed on a corresponding one of said plurality of bridge portions;
    each of said pairs of electrodes is formed on a corresponding one of said plurality of bridge portions;
    said heater means includes a plurality of heater leads; and
    each of said heater leads is formed on a corresponding one of said plurality of bridge portions.

3. A gas detecting device as claimed in claim 2, wherein said bridge portions are parallel with each other, and said electrode leads are parallel with said heater leads.

4. A gas detecting device as claimed in claim 2, wherein said plurality of gas sensitive elements are comprised of an identical material, and wherein said plurality of heater leads pass different amounts of currents so that said plurality of gas sensitive elements are set to different temperatures which are said predetermined temperatures.

5. A gas detecting device as claimed in claim 1, wherein:
    said substrate has a groove formed at a center portion thereof and a single bridge portion formed across said groove;
    said plurality of gas sensitive elements are formed on said single bridge portion;
    said pairs of electrode lead are formed on said single bridge portion;
    said heater means includes a plurality of heater leads; and
    said heater leads are formed on said single bridge portion.

6. A gas detecting device as claimed in claim 5, wherein said plurality of gas sensitive elements are spaced apart from each other and arranged into a line, and said plurality of heater leads include a pair of heater leads which are arranged on sides of said plurality of gas sensitive elements.

7. A gas detecting device as claimed in claim 5, wherein said plurality of gas sensitive elements are comprised of an identical material, and rise to different temperatures which are said predetermined temperatures.

8. A gas detecting device as claimed in claim 1, wherein:
    said substrate has a groove formed at a center portion thereof and a plurality of cantilever portions formed at individual corner portions of said substrate and extending above said groove;
    each of said plurality of gas sensitive elements is formed on a corresponding one of said plurality of cantilever portions;
    each of said pairs of electrode lead is formed on a corresponding one of said plurality of cantilever portions;
    said heater means includes a plurality of heater leads; and
    each of said heater leads is formed on a corresponding one of said plurality of cantilever portions.

9. A gas detecting device as claimed in claim 8, wherein said plurality of gas sensitive elements are comprised of an identical material, and rise to different temperatures which are said predetermined temperatures.

10. A gas detecting device as claimed in claim 8, wherein each of said heater leads is arranged in a parallel manner with a corresponding one of said pairs of electrode leads.

11. A gas detecting device as claimed in claim 1, wherein:
    said substrate has a groove formed at a center portion thereof and a single cantilever formed at a corner portion of said substrate and extending above said groove;
    said plurality of gas sensitive elements are formed on said single cantilever portion;
    said pairs of electrode leads are formed on said single cantilever portion;
    said heater means includes a pair of heater leads provided in common for said plurality of gas sensitive elements; and
    said heater leads are formed on said single cantilever portion.

12. A gas detecting device as claimed in claim 11, wherein said plurality of gas sensitive elements are spaced apart from each other and arranged into a line, and said heater lead is arranged along sides of said single cantilever portion.

13. A gas detecting device as claimed in claim 11, wherein said plurality of gas sensitive elements are comprised of an identical material.

14. A gas detecting device as claimed in claim 1, wherein said plurality of gas sensitive elements comprise an identical material.

15. A gas detecting device as claimed in claim 1, wherein said plurality of gas sensitive elements are set to mutually different temperatures which are said predetermined temperatures.

16. A gas detecting element as claimed in claim 1, wherein some of said plurality of gas sensitive elements are set to an identical temperature which is one of said predetermined temperatures.

* * * * *